(12) United States Patent
Slemker et al.

(10) Patent No.: US 8,057,551 B2
(45) Date of Patent: Nov. 15, 2011

(54) LANYARD SUSPENSION SYSTEM FOR A PROSTHETIC LIMB

(75) Inventors: Tracy C. Slemker, Clayton, OH (US); Scott R. Schall, Englewood, OH (US); David G. Firth, Seattle, WA (US); Steven Steinbarger, Wilmington, OH (US)

(73) Assignee: Prosthetic Design, Inc., Clayton, OH (US)

( * ) Notice: Subject to any disclaimer, the term of this patent is extended or adjusted under 35 U.S.C. 154(b) by 1712 days.

(21) Appl. No.: 11/111,483

(22) Filed: Apr. 21, 2005

(65) Prior Publication Data

US 2005/0256589 A1    Nov. 17, 2005

Related U.S. Application Data

(60) Provisional application No. 60/564,849, filed on Apr. 23, 2004.

(51) Int. Cl.
    *A61F 2/78*    (2006.01)
    *A61F 2/80*    (2006.01)
(52) U.S. Cl. ............................................ 623/36; 623/33
(58) Field of Classification Search ........................ None
    See application file for complete search history.

(56) References Cited

U.S. PATENT DOCUMENTS

| | | | |
|---|---|---|---|
| 41,934 A * | 3/1864 | Monroe | 623/33 |
| 2,666,927 A | 1/1954 | Morheiser | |
| 3,584,835 A * | 6/1971 | White et al. | 24/68 CD |
| 3,922,727 A * | 12/1975 | Bianco | 623/24 |
| 5,061,012 A * | 10/1991 | Parker et al. | 297/467 |
| 5,326,351 A * | 7/1994 | Sarazin | 623/33 |
| 5,368,281 A | 11/1994 | Skyba | |
| 5,722,640 A | 3/1998 | Skyba | |
| 6,797,008 B1 | 9/2004 | Arbogast et al. | |
| 2002/0077705 A1* | 6/2002 | Perkins et al. | 623/36 |
| 2004/0021028 A1* | 2/2004 | Lee | 242/381.6 |
| 2005/0209706 A1* | 9/2005 | Warila | 623/33 |

OTHER PUBLICATIONS

Author Unknown, Alpha Locking Lanyard Fabrication Instructions, Aug. 11, 2003, Ohio Willow Wood, Mt. Sterling, USA.

* cited by examiner

*Primary Examiner* — David H Willse
(74) *Attorney, Agent, or Firm* — Baker & Hostetler LLP

(57) ABSTRACT

A lanyard suspension system for a prosthetic limb that includes: (a) a lanyard cord adapted to extend from a distal end of a patient's residual limb; and (b) a lanyard lock assembly adapted to be seated at a distal end of a patient's prosthetic limb socket assembly. The lanyard lock assembly includes: (1) a lanyard lock base having a lanyard cord channel extending therethrough from an inlet hole in a proximal surface of the lanyard lock base to an outlet hole in one of a side surface and a distal surface of the lanyard lock base; and (2) a locking mechanism designed to allow the lanyard cord to substantially freely thread through the lanyard cord channel from the inlet hole to the outlet hole while substantially inhibiting the lanyard cord from threading in the opposite direction when in an active setting.

28 Claims, 11 Drawing Sheets

LANYARD SUSPENSION SYSTEM FOR A PROSTHETIC LIMB

CROSS REFERENCE TO RELATED APPLICATIONS

The present application claims the benefit of U.S. Provisional Patent Application Ser. No. 60/564,849, filed on Apr. 23, 2004, the disclosure of which is incorporated herein by reference.

BACKGROUND

The present invention relates to a lanyard suspension system for a prosthetic limb; and, more specifically, a lanyard suspension system that may have a lower profile and may be less complicated than other known lanyard suspensions systems.

SUMMARY

The present invention is directed to a lanyard suspension system for a prosthetic limb socket assembly, and components thereof, and methods associated therewith. The lanyard suspension system includes a low-profile locking device adapted to be received within a distal end of a patient's outer prosthetic limb socket. The locking device includes an inlet hole on a proximal surface thereof for receiving the lanyard cord extending from a distal end of an inner, flexible socket worn on a patient's residual limb. The cord is threaded through the locking device and emerges out from an outlet hole of the locking device, and in turn, through an adjacent hole in the outer socket. The locking device is designed to allow the cord to freely thread through the locking device in a first direction—the direction that will pull the patient's residual limb into the outer socket—and is designed to substantially inhibit or lock the cord from threading through the locking device in the opposite direction. This cord locking function greatly assists the patient in donning the outer socket, especially when the residual limb is not easily entirely received within the outer socket (i.e., needs a lot of shifting and adjustment during the donning process).

The locking device includes a release button or mechanism that, when activated, allows the cord to be threaded in both directions, thereby allowing the residual limb to be removed again from the outer socket.

When the residual limb is pulled into the outer socket using the lanyard system, a cord retraction mechanism is provided to wind-up and store the excess lanyard cord extending out from the outer socket within a housing or on a reel, such that the excess cord is conveniently stored therewithin. In the exemplary embodiment, the cord retraction mechanism is a spring loaded winding/reel mechanism similar to an ordinary tape-measure device.

Therefore it is a first aspect of the present invention to provide a lanyard suspension system for a prosthetic limb that includes: (a) a lanyard cord adapted to extend from a distal end of a patient's residual limb; and (b) a lanyard lock assembly adapted to be seated at a distal end of a patient's prosthetic limb socket assembly. The lanyard lock assembly includes: (1) a lanyard lock base having a lanyard cord channel extending therethrough from an inlet hole in a proximal surface of the lanyard lock base to an outlet hole in one of a side surface and a distal surface of the lanyard lock base, where the lanyard cord channel is adapted to receive the lanyard cord extending therethrough; and (2) a locking mechanism designed to allow the lanyard cord to substantially freely thread through the lanyard cord channel from the inlet hole to the outlet hole while substantially inhibiting the lanyard cord to thread in the opposite direction when in an active setting and designed to allow the lanyard cord to freely thread through the lanyard cord channel in both directions when in an inactive setting. In this first aspect, the locking mechanism utilizes at least one biased jaw for engaging with the lanyard cord in the cord channel when the lanyard cord is pulled in the opposite direction in the active setting.

In a more detailed embodiment, the locking mechanism is biased to the active setting. In a further detailed embodiment, the lanyard lock assembly includes a manually actuated release button operatively coupled to the locking mechanism for allowing manual manipulation of the locking mechanism from the active setting to the inactive setting.

Alternatively, the lanyard cord channel includes a lock engaging segment having at least one wall; the biased jaw is a pivotable jaw having at least one tooth adapted to be biased into the lock engaging segment of the lanyard cord channel and against the at least one wall when the locking mechanism is in the active setting, and the pivotable jaw being pivoted so that the at least one tooth moves away from the at least one wall when the locking mechanism is manipulated to the inactive setting; and the at least one tooth is adapted to engage the lanyard cord and press the lanyard cord against the at least one wall in the active setting. In a more detailed embodiment, the pivotable jaw is sized and positioned such the at least one tooth may not be pivoted in the direction of the bias beyond the at least one wall, but is substantially freely pivotable in the opposing direction, against the direction of bias. The lanyard lock assembly may include a manually actuated release button operatively coupled to the pivotable jaw, and the pivotable jaw is pivoted so that the at least one tooth moves away from the at least one wall when the release button is actuated.

In an alternate detailed embodiment of the first aspect of the present invention, the lanyard suspension system further includes (c) a means for retaining slack lanyard cord extending out through the outlet hole. In a further detailed embodiment, the retaining means is located within the lanyard lock base. In yet a further detailed embodiment, the retaining means includes a feed hole for receiving slack lanyard cord; and the lanyard suspension system further comprises (d) a lanyard cord feed-through component adapted to be seated within or to a wall of the patient's prosthetic limb socket assembly adjacent to the outlet hole and the feed hole, where the feed-through component includes: (i) an outlet channel extending from an interior side of the feed-through component to an exterior side of the feed-through component, (ii) an inlet channel extending from an exterior side of the feed-through component to an interior side of the feed-through component, and (iii) a tab extending from the exterior side of the feed-through component in between the inlet channel and the outlet channel, where the tab is adapted to seat a segment of the lanyard cord extending between the inlet channel and outlet channel thereon. With this, a user may grip the segment of the lanyard cord seated on the tab.

It is a second aspect of the present invention to provide a lanyard suspension system for a prosthetic limb that includes: (a) a lanyard cord adapted to extend from a distal end of a patient's residual limb; and (b) a lanyard lock assembly adapted to be coupled to a prosthetic limb assembly. The lanyard lock assembly includes: (1) a lanyard lock base having a lanyard cord channel extending therethrough from an inlet hole of the lanyard lock base to an outlet hole of the lanyard lock base, where the lanyard cord channel is adapted to receive the lanyard cord extending therethrough; and (2) a lanyard cord retraction mechanism including a spool for winding slack lanyard cord extending out through the outlet hole of the lanyard lock base thereabout. In a further detailed embodiment, the spool is biased to rotate in a rotational direction that causes the slack lanyard cord to be wound into the spool.

In an alternate detailed embodiment of the second aspect of the present invention, the lanyard cord retraction mechanism is integrated with the lanyard lock base. In a more detailed embodiment, the lanyard cord retraction mechanism includes a feed hole for receiving slack lanyard cord; and the lanyard suspension system further includes (c) a lanyard cord feed-through component adapted to be coupled adjacent to the outlet hole and the feed hole, where the feed-through component includes: (i) an outlet channel extending from an interior side of the feed-through component to an exterior side of the feed-through component, (ii) an inlet channel extending from an exterior side of the feed-through component to an interior side of the feed-through component, and (iii) a tab extending from the exterior side of the feed-through component in between the inlet channel and the outlet channel, where the tab is adapted to seat a segment of the lanyard cord extending between the inlet channel and outlet channel thereon. With this design, a user may grip the segment of the lanyard cord seated on the tab.

It is a third aspect of the present invention to provide a lanyard suspension system for a prosthetic limb that includes: (a) a lanyard cord adapted to extend from a distal end of a patient's residual limb; and (b) a lanyard lock assembly adapted to be coupled to a prosthetic limb assembly. The lanyard lock assembly includes: (1) a lanyard lock base having a lanyard cord channel extending therethrough from an inlet hole of the lanyard lock base to an outlet hole of the lanyard lock base, where the lanyard cord channel is adapted to receive the lanyard cord extending therethrough; and (2) a locking mechanism designed to allow the lanyard cord to freely thread through the lanyard cord channel from the inlet hole to the outlet hole while substantially inhibiting the lanyard cord to thread in the opposite direction when in an active setting and designed to allow the lanyard cord to freely thread through the lanyard cord channel in both directions when in an inactive setting, where the locking mechanism utilizes at least one biased jaw for engaging with the lanyard cord in the cord channel when the lanyard cord is pulled in the opposite direction in the active setting. In a more detailed embodiment, the locking mechanism is biased to the active setting. In yet a further detailed embodiment, the lanyard lock assembly includes a manually actuated release button operatively coupled to the locking mechanism for allowing manual manipulation of the locking mechanism from the active setting to the inactive setting.

In an alternate detailed embodiment of the third aspect of the present invention, the lanyard suspension system further includes (c) a lanyard cord retraction assembly adapted to hold slack lanyard cord extending out through the outlet hole of the lanyard lock base. In a more detailed embodiment, the lanyard cord retraction assembly includes a spool for winding slack lanyard cord extending out through the outlet hole of the lanyard lock base thereabout.

It is a fourth aspect of the present invention to provide a method for donning a prosthetic limb assembly on a patient's residual limb that includes the steps of: (a) attaching a lanyard cord to a distal end of a patient's residual limb; (b) installing a lanyard lock assembly to a prosthetic limb assembly, the lanyard lock assembly including a lanyard lock base having a lanyard cord channel extending therethrough from an inlet hole of the lanyard lock base to an outlet hole of the lanyard lock base, where the lanyard cord channel is adapted to receive the lanyard cord extending therethrough; (c) threading the lanyard cord into the inlet hole and out through the outlet hole of the lanyard lock base; (d) manually pulling on the lanyard cord extending out through the outlet hole of the lanyard lock base to draw the patient's residual limb to the prosthetic limb assembly; and (e) winding any slack lanyard cord extending out through the outlet hole of the lanyard lock base on a spool positioned approximate to or integrated with the lanyard lock assembly. It is to be understood that the above steps need not proceed in the exact order presented. In a further detailed embodiment, the winding step is automatically performed by a winding mechanism operatively coupled to the spool.

DETAILED DESCRIPTION

Figure 1:
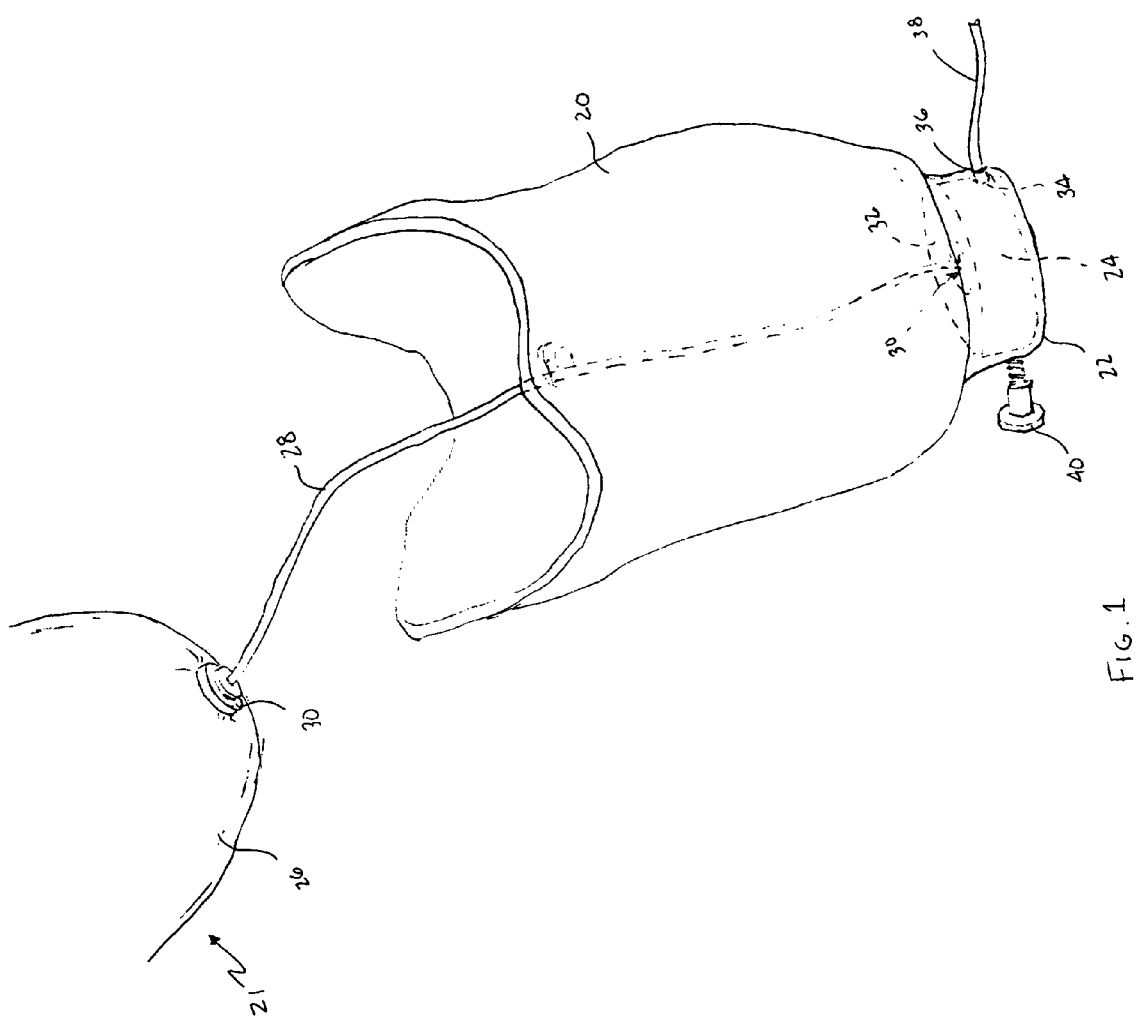
FIG. 1 is a perspective view of an exemplary prosthetic limb socket assembly incorporating an exemplary lanyard suspension system according to an exemplary embodiment of the present invention.

As shown in FIG. 1, an exemplary prosthetic limb socket assembly includes a rigid outer socket 20, typically constructed of a thermoplastic material, shaped for receiving a patient's residual limb 21 therein, where the outer socket component 20 includes a distal extended portion 22 for seating a lanyard lock component 24 therein in accordance with an exemplary embodiment of the present invention. A resilient inner socket 26, typically formed from a silicone material, is donned on the patient's residual limb 21 and includes a lanyard cord 28 extending from an attachment tab 30 threaded to a distal end of the inner socket 26. The lanyard cord 28 extends into a center hole 30 positioned within the concave proximal end 32 of the lanyard lock 24 and extends out through a radial side hole 34 of the lanyard lock 24 and on through a radial side hole 36 bored through the extended portion 22 of the outer socket component 20.

Thus, the patient may grip the distal portion 38 of the lanyard cord extending out through the radial hole 36 and pull on the distal portion 38 of the lanyard cord such that the residual limb 21 is pulled distally towards the concave proximal end 32 of the lanyard lock 24 until the patient's residual limb covered by the inner socket 26 is comfortably and securely received within the outer socket 20. The lanyard lock 24 of the exemplary embodiment is designed such that the cord 28 is freely threaded forwardly through the lanyard lock 24 as described above, but automatically locked from threading rearward back through the lock 24, unless the release button 40 of the lanyard lock is engaged. Therefore, the user can incrementally tug his or her residual limb 21 into the outer socket 20 without worrying about the lanyard cord 28 pulling back out from the lanyard lock 24 as the outer socket 20 is being donned. This is very useful in circumstances where the residual limb has a difficult time being received within the outer socket 20 and the user needs to pull the residual limb into the outer socket to a certain extent by pulling on the distal portion of the lanyard cord 38, walk around or adjust the residual limb a bit such that certain portions of the patient's limb settle within the socket 20, and then pull again on the distal portion 38 of the lanyard cord to further draw in the distal end of the patient's residual limb. Such a donning process could be repeated until the residual limb is snugly and securely received within the outer socket 20.

Of course, to remove the patient's residual limb, the patient merely activates the release button 40, thereby unlocking the lanyard cord 28 within the lanyard lock 24 and then pulls his or her residual limb 21 out again from the outer socket 20. At that point, the connection tab 30 can be unscrewed from the inner socket 26 to release the residual limb 21 from the lanyard system.

Figure 2:
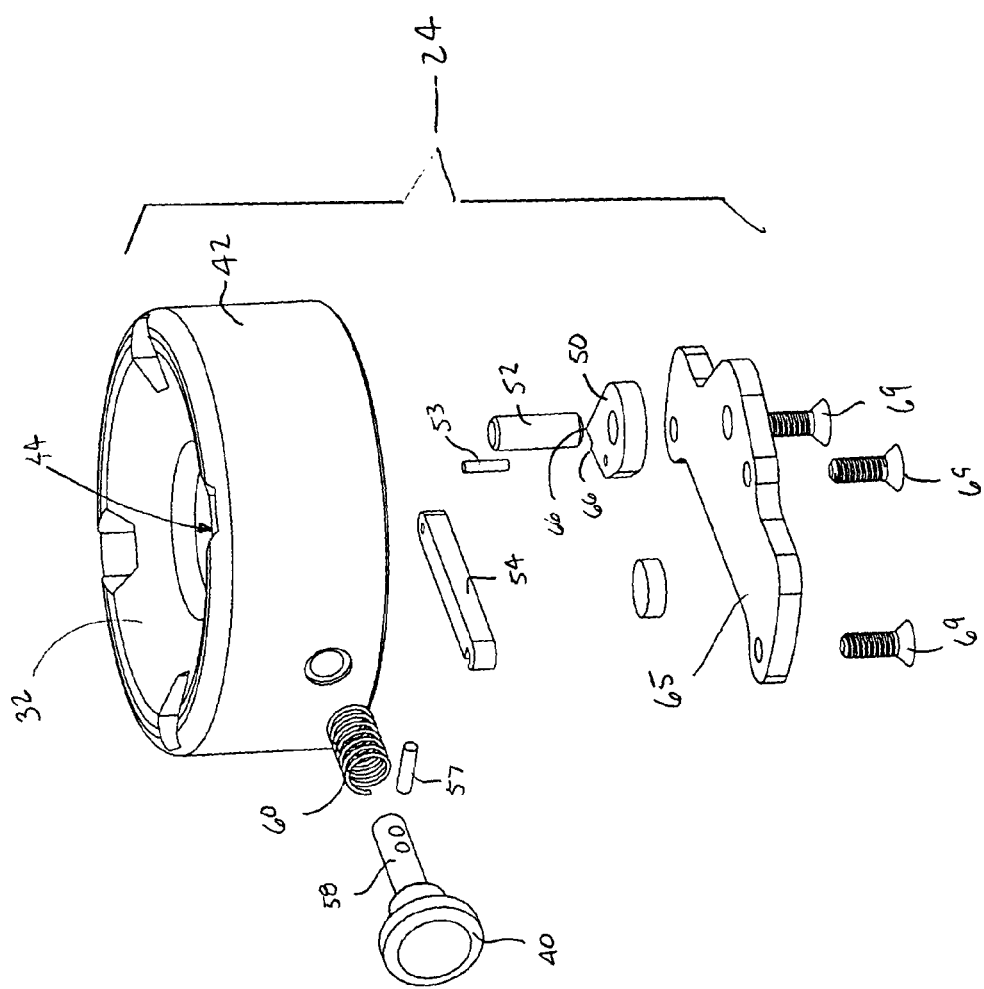
FIG. 2 is an exploded, perspective view of a lanyard lock for use with the exemplary embodiment of FIG. 1.
Figure 3:
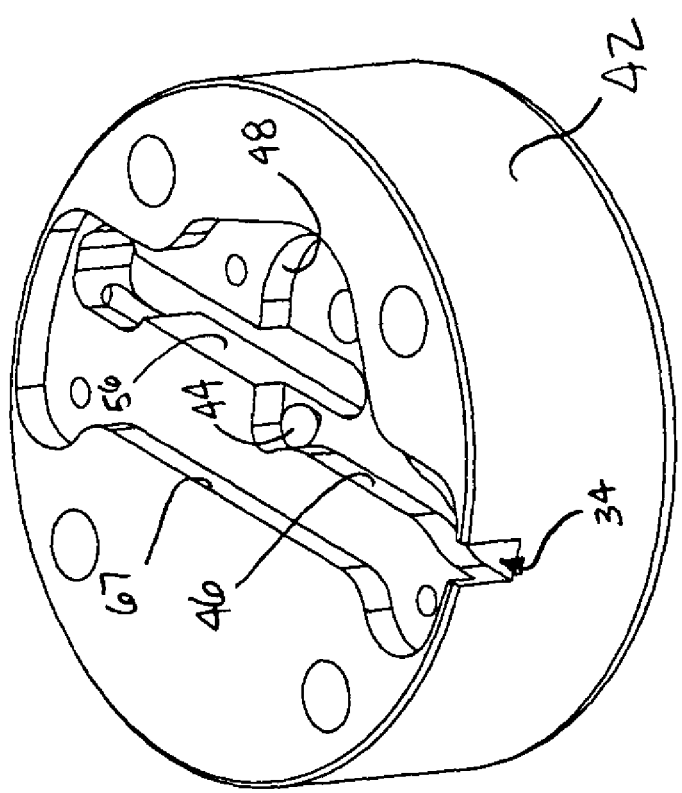
FIG. 3 is a perspective, under-side view of the base component of the Lanyard Lock of FIG. 2.
Figure 4:
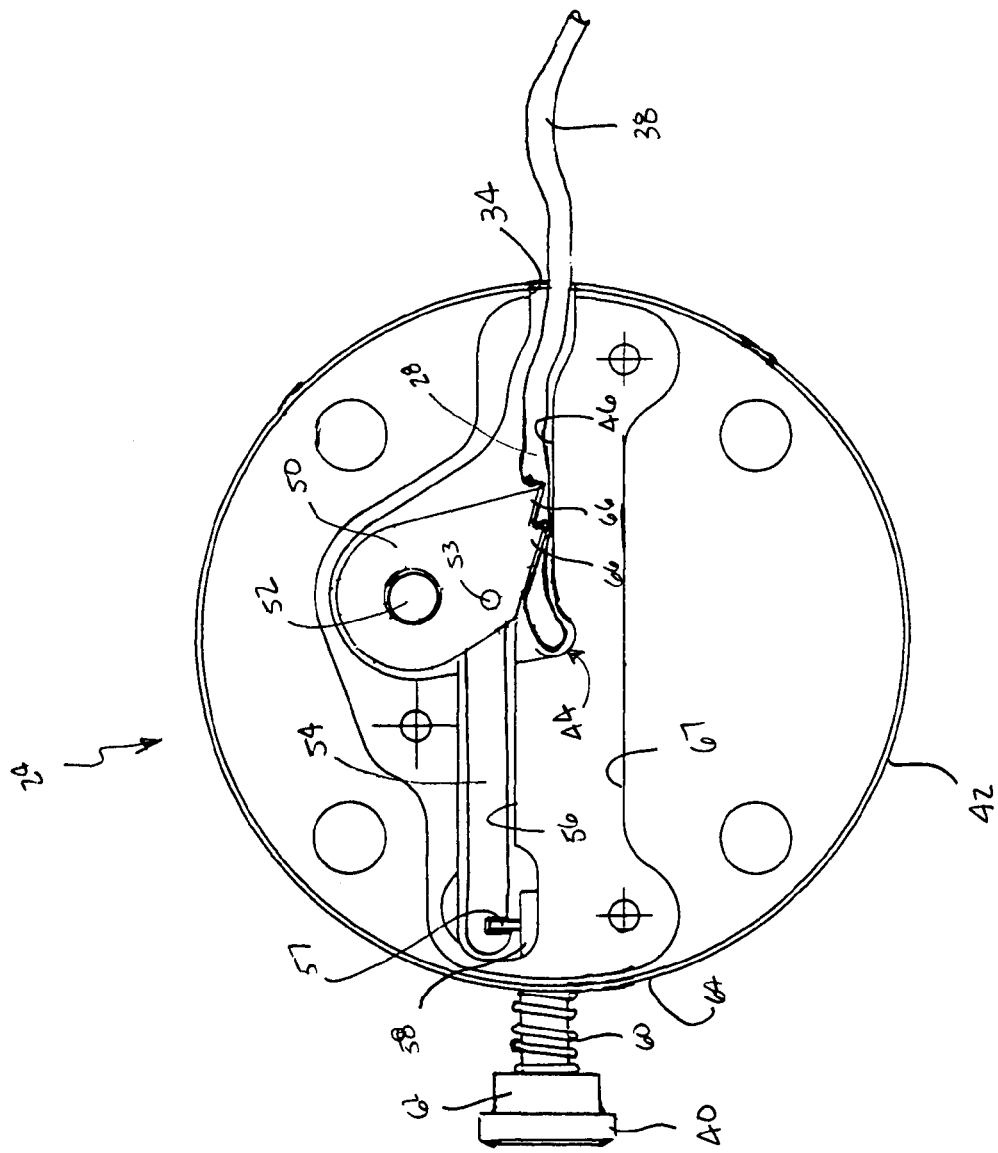
FIG. 4 is an under-side view of the lanyard lock of FIG. 2 (without the cover), shown in the locked position.

As shown in FIGS. 2-4, the exemplary lanyard lock 24 includes a substantially cylindrical base component 42 having a concave proximal surface 32 and including a center hole 44 provided at the center of the concave surface for receiving the lanyard cord 28 therein. As shown best in FIG. 3, the hole 44 opens distally on a cord channel 46 bored in the distal end of the base 42 where the cord channel 46 extends radially out and opens at the radial cord outlet opening 34. This cord channel 46 includes a substantially round expanded portion 48 for seating a pivoting jaw 50 and its associated pivot pin 52 therein. The pivoting jaw 50 is also pivotally coupled to an elongated link bar 54 at an off-center point on the pivoting jaw 50 by a pin 53. The link bar 54 can reciprocate in a radial channel 56 that extends below the cord channel 46 in a radial direction generally away from the opening 34. A pin 57 couples the link bar 54 in parallel to an actuation post 58 of the release button 40 extending into a radial end of the base 42 opposing the cord opening 34. A spring 60 is provided on the post 58 radially between a head 62 of the release button and an outer cylindrical wall 64 of the base 42 so as to bias the release button 40 radially outwardly from the base 42. This bias, in turn, biases the link bar 54 in a radial direction towards the release button 40 (away from the cord outlet 34), which in turn biases the jaw 50 to rotate clockwise such that the teeth 66 of the jaw grip and press the cord 28 extending through the cord channel 46 against a side wall of the cord channel 46. The above-described locking mechanisms are covered by a cover 65 received flush within a recess 67 bored into the distal end of the base 42 and secured by screws 69.

As can be shown in FIG. 4, if a user were to pull on the distal portion 38 of the cord, the cord would pull the teeth 66 in the jaw 50 counter-clockwise (because the teeth 66 are gripping into the cord 28) and, in turn, release the teeth 66 from the cord 28 within the lock 24 so that the cord 28 may be freely threaded through the lock 24. Conversely, if the user were to pull on the opposite end of the cord, such pulling would further pivot the jaw 50 clockwise, further locking the teeth 66 with the cord 28 against the side wall of the cord channel 46.

Figure 5:
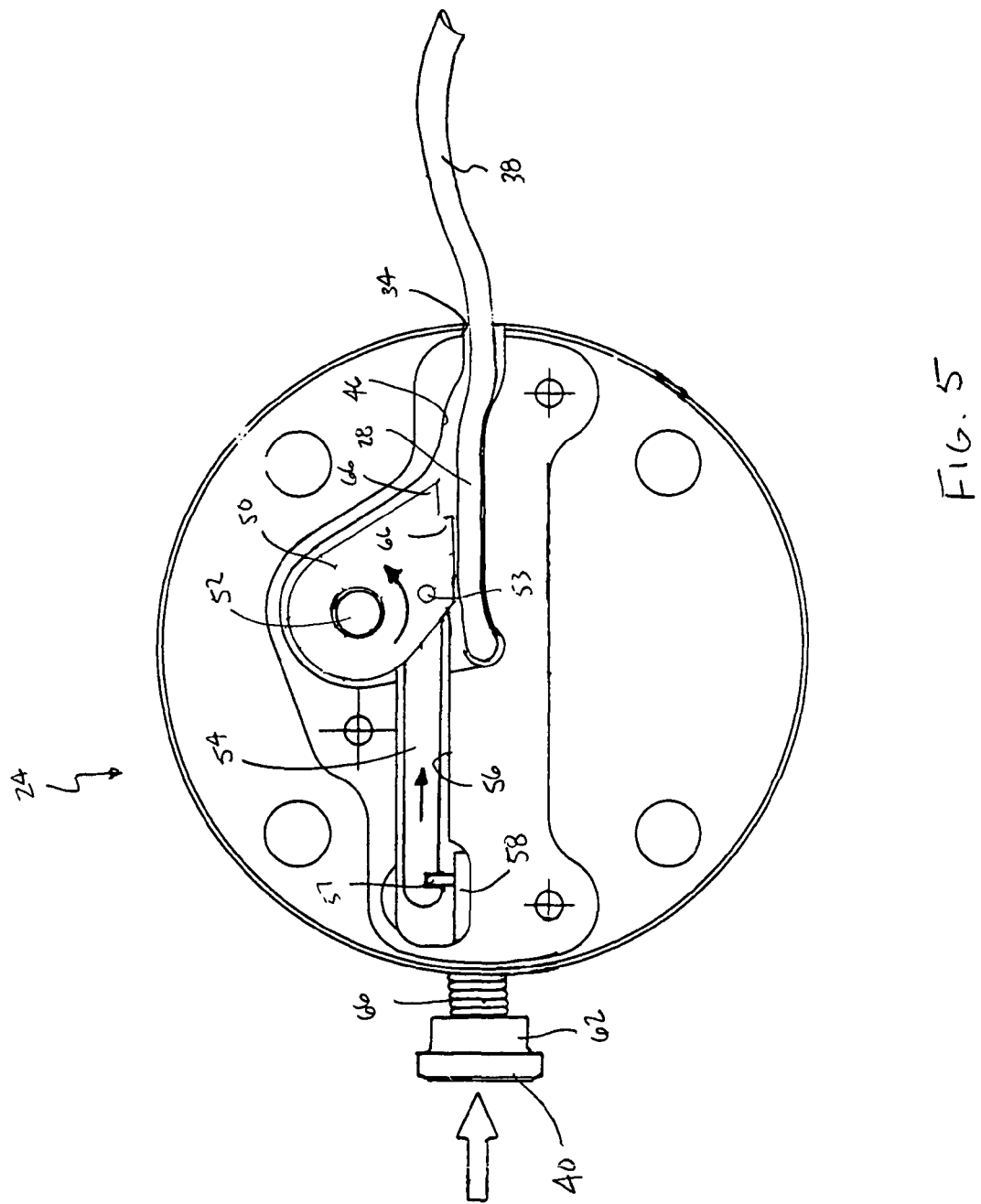
FIG. 5 is an under-side view of the lanyard lock of FIG. 2 shown in the unlocked position.

As shown in FIG. 5, when the release button is pressed radially inwardly by the patient, the radially inward movement of the link bar 54 causes the jaw 50 to rotate counter-clockwise, thereby moving the teeth 66 out of the path of the cord 28. This, in turn, allows the cord 28 to thread freely in either a forward or backward direction within the cord channel 46.

In the exemplary embodiment, the design of the lanyard lock 24 allows it to have a low profile of ½", weighing approximately 3.8 oz. Furthermore, the lanyard lock 24 design allows it to be accommodated by using conventional lock tools provided by Prosthetic Design Inc., such as SSFT, DLP-KIT, FET-KIT. Finally, the design of the lanyard lock 24 allows to be retrofit with Xtreme and Pro Locks commercially available from Prosthetic Design, Inc.

Figure 6:
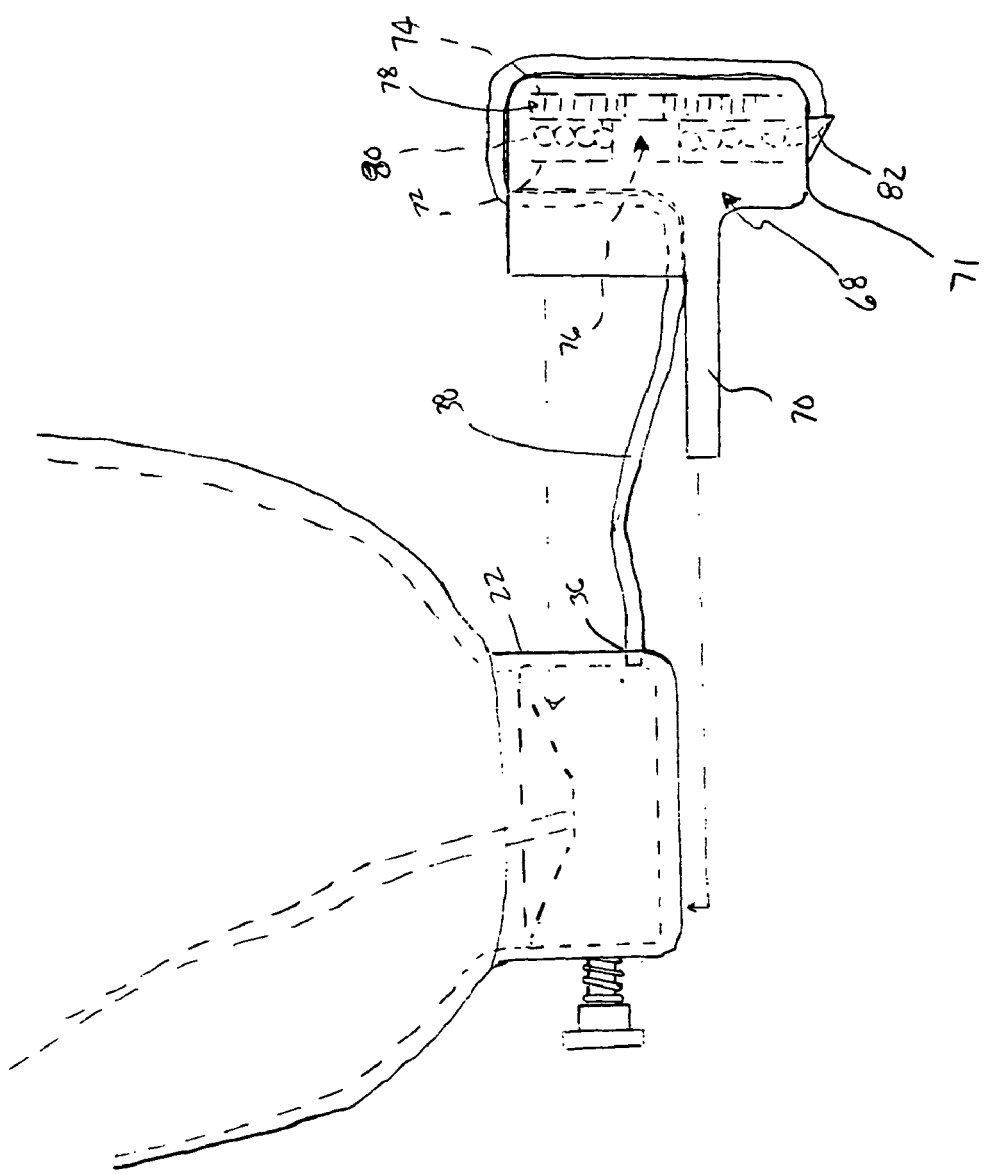
FIG. 6 is an elevational side view of the prosthetic limb socket assembly and lanyard suspension systems of FIGS. 1-5 incorporating an exemplary embodiment of a lanyard cord winding mechanism.
Figure 7:
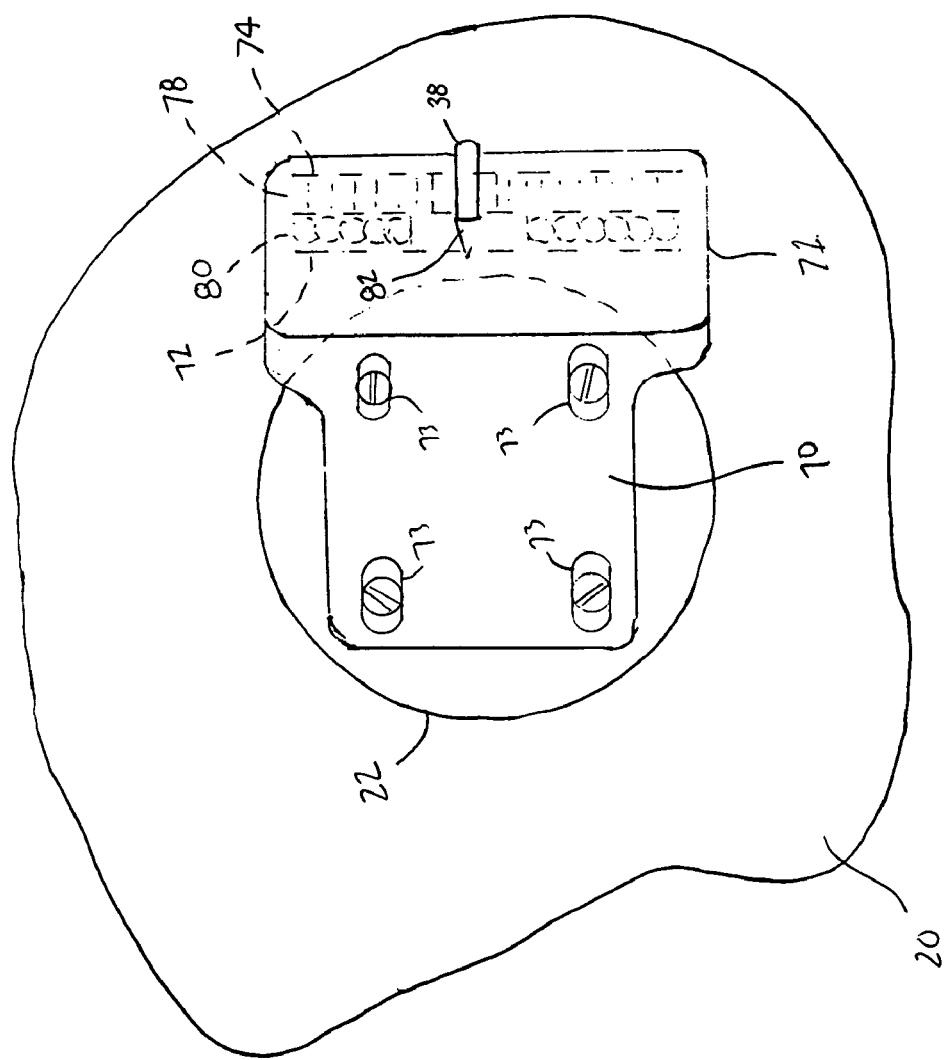
FIG. 7 is an under-side view of the prosthetic limb socket assembly having the lanyard cord winding mechanism of FIG. 6 mounted to an under-side thereof.

As shown in FIGS. 6 and 7, a first exemplary embodiment of an automatic cord retraction mechanism 68 for retaining the slack of the distal end 38 of the lanyard cord includes an attachment plate portion 70 for mounting to the distal end of outer socket's extended portion 22, and a main body portion 71 housing the winding mechanisms for automatically retracting the slack distal end 38 of the lanyard cord when the user is no longer gripping it. The attachment plate portion 70 includes a standard 4-hole attachment pattern, where the holes are slotted to allow the mechanism 68 to be drawn against the circumference of the outer socket extended portion 22. The body portion 71 of the mechanism 68 is also contoured to integrate with the outer socket extended portion 22 so as to help prevent accidental catch on other object.

The retraction mechanism 68 includes a cord spool 72 coaxially mounted to a spring reel 74 on a rotational hinge or axis 76. The spring reel 74 contains a constant force spring 78 wound thereon, where one end of the constant force spring is attached to the hub of the reel 74 and the other end of the constant force spring is attached at an outer periphery of the reel 74. The cord spool 72 contains slack portion of the cord 38 wound thereon, which feeds into and out from the winding housing 71 from an outer opening 82. To provide the patient access to the lanyard cord 38, the cord 38 feeds out from the opening 82, over the body portion 71, and into the cord hole 36 bored in the side of the extended portion 22 of the outer socket 20. The winder operates such that when the patient pulls slack cord out from the winder housing 68 causing the cord spool 72 and spring reel 74 to rotate in a first direction, the spring 78 will build a centrifugal kinetic force such that when the cord is released again the kinetic force built into the spring 78 will cause the spool and reel 72, 74 to spin in the opposite direction, thereby causing the slack cord to wind again around the cord spool 72.

Figure 8:
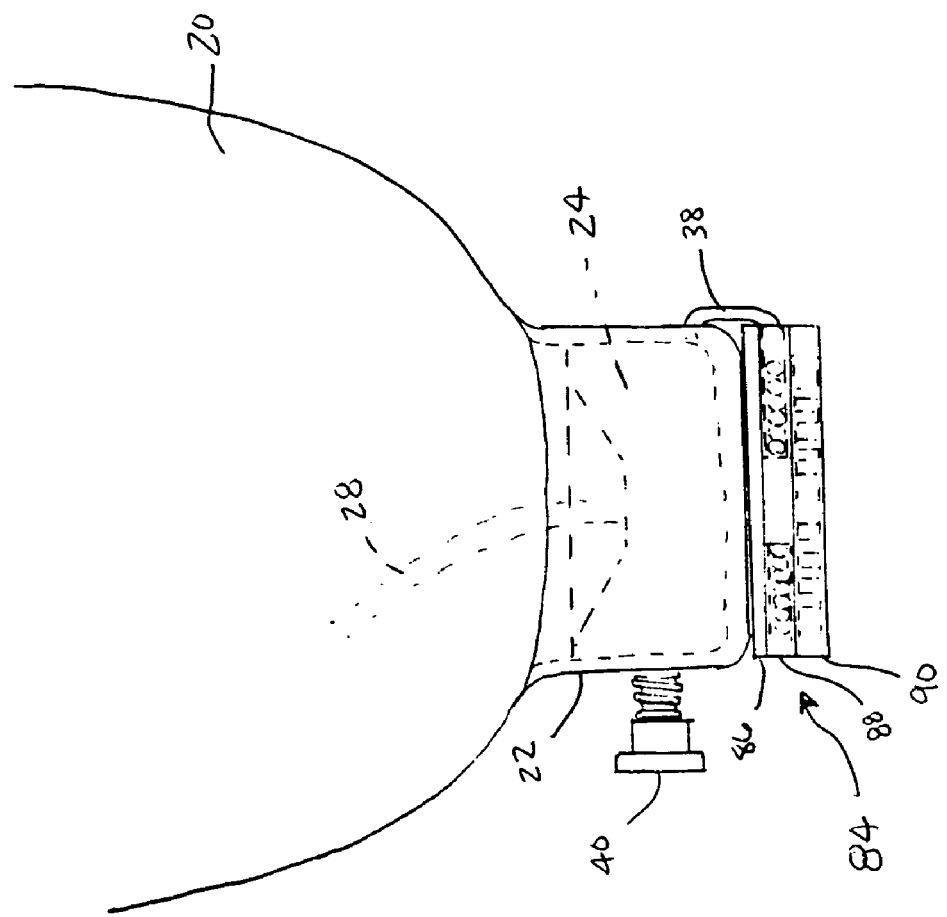
FIG. 8 is an elevational side view of an alternate exemplary embodiment of a lanyard cord winding mechanism.
Figure 9:
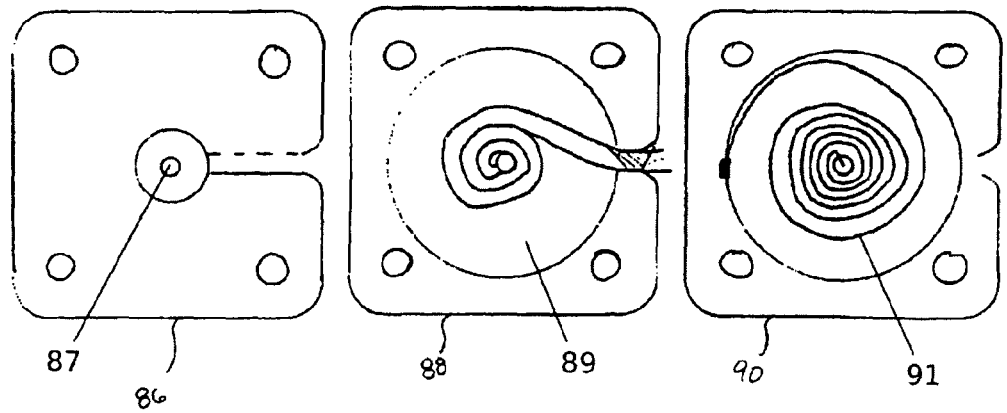
FIG. 9 is a top plan view of three plate components of the winding mechanism shown in FIG. 8.

FIGS. 8 and 9 illustrate an embodiment of a cord retraction mechanism built into a four-hole extender plate 84 mounted to a distal end of the prosthetic limb outer socket. The extender plate includes three sub-plates, a top plate 86; a middle, cord spool plate 88 including a spool 89 for winding up the slack cord; and a lower, spring plate 90 including a constant force spring 91 coupled to the spool plate 88 by a pin 87 extending axially through the middle plate 88 and rotationally seated in the top and lower plates 86, 90. As will be recognized by one of ordinary skill in the art, the extender plate embodiment of FIGS. 8 and 9, operates in a similar manner to the winder mechanism described above with respect to FIGS. 6 and 7.

Figure 10:
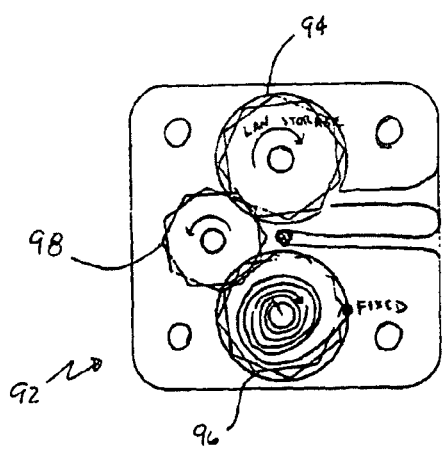
FIG. 10 is an another alternate winding mechanism utilizing fewer plates than the mechanism of FIGS. 8 and 9.

FIG. 10 illustrates a single plate embodiment 92 of the extender plate cord retraction mechanism described above with FIGS. 8 and 9. In this embodiment 92, the cord spool 94 and spring reel 96 are both provided on the same plate and are coupled to each other for simultaneous rotation by a gear assembly 98.

Figure 11:
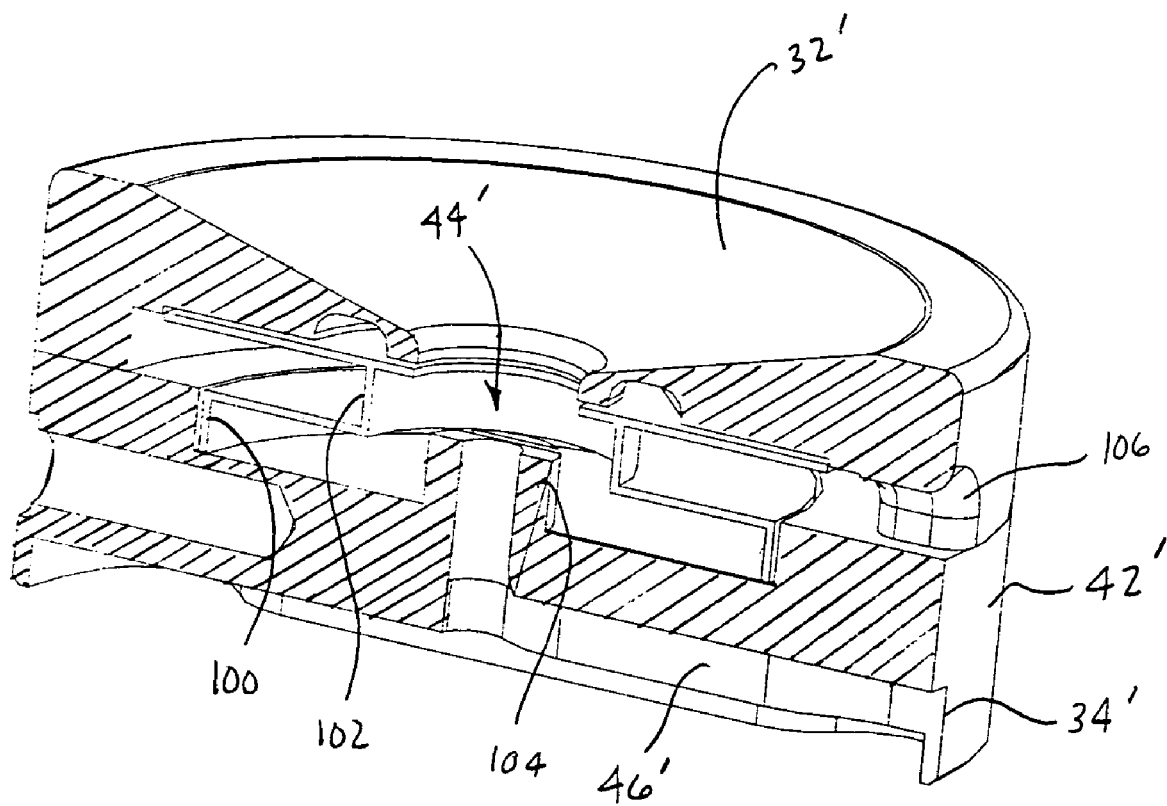
FIG. 11 is a perspective, cross-sectional view of a base component of an embodiment of a lanyard lock incorporating a winding mechanism therein.

FIG. 11 illustrates a cord retraction mechanism built into the lanyard lock embodiment described in FIG. 1-5 above. In this embodiment, the base 42 includes a spring reel 100 and a cord spool 102 coaxially mounted therewithin about a hinge 104, through which the cord hole 44' extends into the cord channel 46'. Cord slack 38 is fed from the radial side opening 34', out through the adjacent outer socket wall, over a D-shaped gripping tab as described below, back into the outer socket wall, and back into the cord spool 102 through a radial side hole 106.

Figure 13:
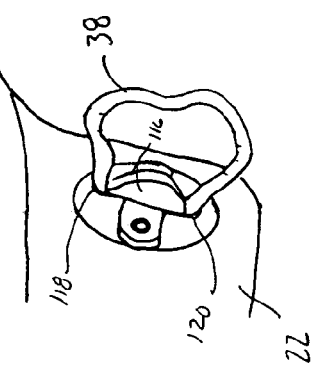
FIG. 13 is an assembled view of the lanyard cord gripping assembly as incorporated into a prosthetic limb socket component.
Figure 12:
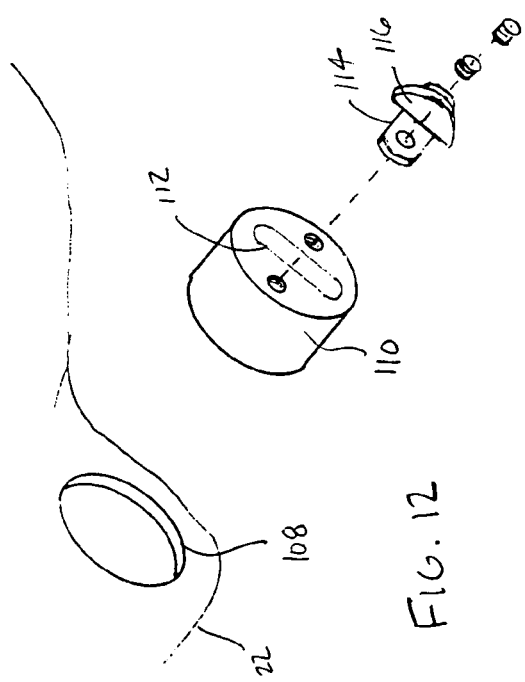
FIG. 12 is an exploded view of a lanyard cord gripping assembly for use with the embodiment of FIG. 11.

FIGS. 12 and 13 illustrate a gripping assembly for allowing user to grip the cord 38 threaded out from the side hole 34' and back into the feed hole 106 as shown in FIG. 11. A hole 108 is bored into the radial side of the extended portion 22 of the outer socket adjacent to the outlet hole 34' and inlet hole 106. A feed-through component 110 which includes a diametric channel 112 extending therethrough is mounted in the hole 108. A D-shaped tab component 114 is mounted over the channel 112 such that the D-shaped tab portion 116 of the component 114 leaves upper and lower openings 118, 120 for a loop of the cord 38 to extend out through. When the excess cord is reeled into the cord retraction mechanism shown in FIG. 11, the D-shaped tab 116 retains a portion of the loop of cord 38 thereover allowing the user to easily grip the loop and pull on the cord.

It will be appreciated that with the above-described cord retraction mechanisms that the springs can be replaced with powered winders. It will also be appreciated that the force of the springs or the powered winders could be such that the need for the patient to pull on the distal section of cord 38 when donning the outer socket 22 is reduced or eliminated (i.e., sufficient pull could be provided by the retraction mechanisms themselves). In such embodiments, it might not be necessary to feed a portion of the distal cord 38 out from the socket for the patient to grip and pull on (i.e., the distal portion of cord 38 can be completely contained within the lock/winding mechanism).

Following from the above detailed description, it will be apparent to those of ordinary skill in the art that, while the apparatuses and processes herein described constitute exemplary embodiments of the present invention, it is understood that the invention is not limited to these precise apparatuses and processes and that changes may be made therein without departing from the scope of the invention as claimed or as illustrated by the various aspects of the present invention set forth in the summary. Additionally, it is to be understood that the invention is defined by the claims and it is not intended that any limitations or elements describing the exemplary embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A lanyard suspension system for a prosthetic limb, the prosthetic limb including a prosthetic limb socket component having an interior and an inner surface, the lanyard suspension system comprising:

a lanyard cord adapted to extend from a distal end of a patient's residual limb, the lanyard cord having a substantially circular cross section; and a lanyard lock assembly sized and shaped to be seated within the interior of the prosthetic limb socket component, between the inner surface of the prosthetic limb socket component and the patient's residual limb, at a distal end of a patient's prosthetic limb socket component, the lanyard lock assembly including a substantially cylindrical lanyard lock base, sized and shaped to be removably mounted entirely within the interior of the prosthetic limb socket component, and having a lanyard cord channel extending therethrough from an inlet hole in a substantially circular, at least partially concave proximal surface of the lanyard lock base to an outlet hole in one of a side surface and a generally circular distal surface of the lanyard lock base, wherein the lanyard cord channel is adapted to receive the lanyard cord extending therethrough;

a locking mechanism provided within the lanyard lock base, the locking mechanism being designed to allow the lanyard cord to substantially freely thread through the lanyard cord channel from the inlet hole to the outlet hole while substantially inhibiting the lanyard cord to thread in the opposite direction when in an active setting and designed to allow the lanyard cord to freely thread through the lanyard cord channel in both directions when in an inactive setting, the locking mechanism acting on a portion of the lanyard cord within the lanyard cord channel of the lanyard lock base; and a cord retraction mechanism including a spool operative to receive slack lanyard cord thereabout via a feed hole, the slack lanyard cord extending between the outlet hole and the feed hole;

the locking mechanism utilizing at least one biased jaw provided completely within the lanyard lock base for engaging with the lanyard cord in the cord channel when the lanyard cord is pulled in the opposite direction in the active setting; and wherein the lanyard cord extends from the distal end of the patient's residual limb, through the inlet hole in the proximal surface of the lanyard lock base, through the lanyard cord channel of the lanyard lock base, through the outlet hole in one of the side surface and the distal surface of the lanyard lock base, through the feed hole of the cord retraction mechanism, and to the spool of the cord retraction mechanism.

2. The lanyard suspension system of claim 1 wherein the locking mechanism is biased to the active setting.

3. The lanyard suspension system of claim 2 wherein the lanyard lock assembly includes a manually actuated release button extending radially out from the lanyard lock base and adapted to extend out through the prosthetic limb socket component, the release button being operatively coupled to the locking mechanism for allowing manual manipulation of the locking mechanism from the active setting to the inactive setting.

4. The lanyard suspension system of claim 2 wherein:

the lanyard cord channel includes a lock engaging segment having at least one wall;

the biased jaw is a pivotable jaw having at least one tooth adapted to be biased into the lock engaging segment of the lanyard cord channel and against the at least one wall when the locking mechanism is in the active setting, and the pivotable jaw being pivoted so that the at least one tooth moves away from the at least one wall when the locking mechanism is manipulated to the inactive setting;

the at least one tooth being adapted to engage the lanyard cord and press the lanyard cord against the at least one wall in the active setting.

5. The lanyard suspension system of claim 4, wherein the pivotable jaw is sized and positioned such the at least one tooth may not be pivoted in the direction of the bias beyond the at least one wall, but is substantially freely pivotable in the opposing direction, against the direction of bias.

6. The lanyard suspension system of claim 4, wherein the lanyard lock assembly includes a manually actuated release button operatively coupled to the pivotable jaw, and the pivotable jaw is pivoted so that the at least one tooth moves away from the at least one wall when the release button is actuated.

7. The lanyard suspension system of claim 1, wherein:

the lanyard suspension system further comprises a lanyard cord feed-through component adapted to be seated within or to a wall of the patient's prosthetic limb socket component adjacent to the outlet hole and the feed hole, the feed-through component including an outlet channel extending from an interior side of the feed-through component to an exterior side of the feed-through component, an inlet channel extending from an exterior side of the feed-through component to an interior side of the feed-through component, and a tab extending from the exterior side of the feed-through component in between the inlet channel and the outlet channel, the tab being adapted to seat a segment of the lanyard cord extending between the inlet channel and outlet channel thereon, whereby a user may grip the segment of the lanyard cord seated on the tab.

8. The lanyard suspension system of claim 1, wherein the cord retraction mechanism comprises a spring reel and a cord spool.

9. The lanyard suspension system of claim 1, wherein the lanyard cord includes a threaded attachment tab for coupling with a distal end of an inner socket donned on the patient's residual limb.

10. A lanyard suspension system for a prosthetic limb, the prosthetic limb including a prosthetic limb socket component having an interior and an inner surface, the lanyard suspension system comprising:

a lanyard cord adapted to extend from a distal end of a patient's residual limb, the lanyard cord having a substantially circular cross section; and a substantially cylindrical lanyard lock assembly sized and shaped to be mounted within a distal extended portion of the prosthetic limb socket component, between the inner surface of the prosthetic limb socket component and the patient's residual limb, the lanyard lock assembly including a lanyard lock base having a lanyard cord channel extending therethrough from an inlet hole in a substantially circular, at least partially concave proximal surface of the lanyard lock base to an outlet hole of the lanyard lock base, wherein the lanyard cord channel is adapted to receive the lanyard cord extending therethrough; and a lanyard cord retraction mechanism including a spool for winding slack lanyard cord extending out through the outlet hole of the lanyard lock base thereabout and a spring arranged to bias the spool to rotate in a rotational direction that causes the slack lanyard cord to be wound into the spool;

wherein the lanyard lock assembly is configured to allow the lanyard cord to substantially freely thread through the lanyard cord channel from the inlet hole to the outlet hole while substantially inhibiting the lanyard cord to thread in the opposite direction when in an active setting and designed to allow the lanyard cord to freely thread through the lanyard cord channel in both directions when in an inactive setting.

11. The lanyard suspension system of claim 10, wherein the lanyard cord retraction mechanism is integrated with the lanyard lock base.

12. The lanyard suspension system of claim 11, wherein:

the lanyard cord retraction mechanism includes a feed hole for receiving slack lanyard cord; and the lanyard suspension system further comprises a lanyard cord feed-through component adapted to be coupled adjacent to the outlet hole and the feed hole, the feed-through component including an outlet channel extending from an interior side of the feed-through component to an exterior side of the feed-through component, an inlet channel extending from an exterior side of the feed-through component to an interior side of the feed-through component, and a tab extending from the exterior side of the feed-through component in between the inlet channel and the outlet channel, the tab being adapted to seat a segment of the lanyard cord extending between the inlet channel and outlet channel thereon, whereby a user may grip the segment of the lanyard cord seated on the tab.

13. The lanyard suspension system of claim 10, wherein the lanyard cord includes a threaded attachment tab for coupling with a distal end of an inner socket donned on the patient's residual limb.

14. A lanyard suspension system for a prosthetic limb, the prosthetic limb including a prosthetic limb socket component having an interior and an inner surface, the lanyard suspension system comprising:

a lanyard cord adapted to extend from a distal end of a patient's residual limb;

a lanyard lock assembly adapted to be coupled to a prosthetic limb assembly, the lanyard lock assembly including a cylindrical lanyard lock base, sized to be removably seated entirely within the interior of the prosthetic limb socket component between the inner surface thereof and the patient's residual limb, the cylindrical lanyard lock base having a lanyard cord channel extending therethrough from an inlet hole in a substantially circular proximal surface of the cylindrical lanyard lock base to an outlet hole of the cylindrical lanyard lock base, the lanyard cord channel extending axially through at least a portion of the cylindrical lanyard lock base, wherein the lanyard cord channel is adapted to receive the lanyard cord extending therethrough, and a locking mechanism provided within the cylindrical lanyard lock base and designed to allow the lanyard cord to freely thread through the lanyard cord channel from the inlet hole to the outlet hole while substantially inhibiting the lanyard cord to thread in the opposite direction when in an active setting and designed to allow the lanyard cord to freely thread through the lanyard cord channel in both directions when in an inactive setting; and a spring-biased lanyard cord retraction assembly adapted to hold slack lanyard cord extending out through the outlet hole of the lanyard lock base;

the locking mechanism utilizing at least one biased jaw positioned entirely within the cylindrical lanyard lock base for engaging with the lanyard cord in the cord channel when the lanyard cord is pulled in the opposite direction in the active setting, the at least one biased jaw being biased into the cord channel.

15. The lanyard suspension system of claim 14 wherein the locking mechanism is biased to the active setting.

16. The lanyard suspension system of claim 15 wherein the lanyard lock assembly includes a manually actuated release button extending radially outward from a side of the cylindrical lanyard lock base, the manually actuated release button being operatively coupled to the locking mechanism for allowing manual manipulation of the locking mechanism from the active setting to the inactive setting.

17. The lanyard suspension system of claim 14, wherein the spring-biased lanyard cord retraction assembly includes a spool for winding slack lanyard cord extending out through the outlet hole of the lanyard lock base thereabout.

18. The lanyard suspension system of claim 14, wherein the lanyard cord channel extends radially outward through the cylindrical lanyard lock base.

19. The lanyard suspension system for a prosthetic limb of claim 14, wherein the lanyard cord includes a threaded attachment tab for coupling with a distal end of an inner socket donned on the patient's residual limb.

20. A method for donning a prosthetic limb assembly on a patient's residual limb, the prosthetic limb assembly including a prosthetic limb socket having an interior and an inner surface, the method comprising the steps of:

attaching a lanyard cord to a distal end of a patient's residual limb, the lanyard cord having a substantially circular cross section;

installing a lanyard lock base of a lanyard lock assembly within the interior of the prosthetic limb socket at a distal end of the socket and against the inner surface of the socket, the socket being adapted to receive at least a portion of the patient's residual limb, the lanyard lock base having a lanyard cord channel extending therethrough from an inlet hole of the lanyard lock base to an outlet hole of the lanyard lock base, wherein the lanyard cord channel is adapted to receive the lanyard cord extending therethrough, the socket including a socket outlet hole in communication with the outlet hole of the lanyard lock base, wherein the lanyard lock assembly includes a locking mechanism mounted substantially entirely within the lanyard lock base and acting on a portion of the lanyard cord within the lanyard cord channel of the lanyard lock base, the locking mechanism including at least one biased jaw configured to allow the lanyard cord to substantially freely thread through the lanyard cord channel from the inlet hole to the outlet hole while substantially inhibiting the lanyard cord to thread in an opposite direction while the locking mechanism is in an active setting;

threading the lanyard cord into the inlet hole, out through the outlet hole of the lanyard lock base, and through the socket outlet hole;

manually pulling on the lanyard cord extending out through the outlet hole of the lanyard lock base to draw the lanyard cord through the lanyard cord channel to draw the patient's residual limb to the prosthetic limb assembly; and winding any slack lanyard cord extending out through the outlet hole of the lanyard lock base on a spool positioned approximate to or integrated with the lanyard lock assembly.

21. The method of claim 20, wherein the winding step is automatically performed by a winding mechanism operatively coupled to the spool.

22. The method for donning a prosthetic limb assembly of claim 20, wherein the operation of attaching a lanyard cord to the distal end of the patient's residual limb includes threadedly coupling an attachment tab on the lanyard cord with a distal end of an inner socket donned on the patient's residual limb.

23. A prosthetic limb assembly comprising:

(a) a substantially rigid socket sized and shaped to receive and support a patient's residual limb therein, the socket having an interior and an inner surface and a lanyard cord hole approximate a distal end of the socket;

(b) a lanyard suspension system including
(i) a lanyard cord adapted to extend from a distal end of the patient's residual limb, the lanyard cord having a substantially circular cross section, and
(ii) a lanyard lock assembly including
a lanyard lock base removably seated within the interior of the socket against the inner surface of the socket and at the distal end of the socket, the lanyard lock base having a lanyard cord channel extending therethrough from an inlet hole in a substantially circular, at least partially concave proximal surface of the lanyard lock base to an outlet hole in one of a side surface and a generally circular distal surface of the lanyard lock base, wherein the lanyard cord channel is adapted to receive the lanyard cord extending therethrough, and
a locking mechanism provided within the lanyard lock base, the locking mechanism being designed to allow the lanyard cord to substantially freely thread through the lanyard cord channel from the inlet hole to the outlet hole while substantially inhibiting the lanyard cord to thread in the opposite direction when in an active setting and designed to allow the lanyard cord to freely thread through the lanyard cord channel in both directions when in an inactive setting, the locking mechanism acting on a portion of the lanyard cord within the lanyard cord channel of the lanyard lock base,
the locking mechanism utilizing at least one biased jaw provided entirely within the lanyard lock base for engaging with the lanyard cord in the cord channel when the lanyard cord is pulled in the opposite direction in the active setting; and (c) an upright assembly coupled to the distal end of the substantially rigid socket.

24. The prosthetic limb assembly of claim 23 wherein the lanyard lock assembly includes a manually actuated release button extending radially out from the lanyard lock base and extending out through a release button hole in the socket, the release button being operatively coupled to the locking mechanism for allowing manual manipulation of the locking mechanism from the active setting to the inactive setting.

25. The prosthetic limb assembly of claim 23, wherein the lanyard lock assembly further includes a lanyard cord retraction mechanism including a spool for winding slack lanyard cord extending out through the outlet hole of the lanyard lock base thereabout and a spring arranged to bias the spool to rotate in a rotational direction that causes the slack lanyard cord to be wound into the spool.

26. The prosthetic limb assembly of claim 25, wherein the spool is integrated within the lanyard lock base.

27. The prosthetic limb assembly of claim 25, wherein the lanyard cord retraction mechanism is mounted to an outer surface of the socket approximate a distal end thereof.

28. A lanyard suspension system for a prosthetic limb comprising:
- a lanyard cord adapted to extend from a distal end of a patient's residual limb; and
- a lanyard lock assembly adapted to be seated substantially within a distal end of a patient's prosthetic limb socket assembly, the lanyard lock assembly including
  - a lanyard lock base having a lanyard cord channel extending therethrough from an inlet hole in a proximal surface of the lanyard lock base to an outlet hole in one of a side surface and a distal surface of the lanyard lock base, wherein the lanyard cord channel is adapted to receive the lanyard cord extending therethrough;
  - a locking mechanism designed to allow the lanyard cord to substantially freely thread through the lanyard cord channel from the inlet hole to the outlet hole while substantially inhibiting the lanyard cord to thread in the opposite direction when in an active setting and designed to allow the lanyard cord to freely thread through the lanyard cord channel in both directions when in an inactive setting; and
  - a cord retraction mechanism operative to receive slack lanyard cord through a feed hole, the slack lanyard cord extending between the outlet hole and the feed hole;
- the locking mechanism utilizing at least one biased jaw for engaging with the lanyard cord in the cord channel when the lanyard cord is pulled in the opposite direction in the active setting;
- wherein the lanyard suspension system further comprises a lanyard cord feed-through component adapted to be seated within or to a wall of the patient's prosthetic limb socket assembly adjacent to the outlet hole and the feed hole, the feed-through component including an outlet channel extending from an interior side of the feed-through component to an exterior side of the feed-through component, an inlet channel extending from an exterior side of the feed-through component to an interior side of the feed-through component, and a tab extending from the exterior side of the feed-through component in between the inlet channel and the outlet channel, the tab being adapted to seat a segment of the lanyard cord extending between the inlet channel and outlet channel thereon, whereby a user may grip the segment of the lanyard cord seated on the tab.

* * * * *